United States Patent
Xiao et al.

(10) Patent No.: US 9,227,906 B2
(45) Date of Patent: Jan. 5, 2016

(54) BENZENE RING CONTAINING COMPOUND, SEALING GEL, PROCESS FOR PREPARING SAME AND USE THEREOF

(71) Applicant: BEIJING BOE OPTOELECTRONICS TECHNOLOGY CO., LTD., Beijing (CN)

(72) Inventors: Ang Xiao, Beijing (CN); Sunghun Song, Beijing (CN); Haibo Zhu, Beijing (CN)

(73) Assignee: BEIJING BOE OPTOELECTRONICS TECHNOLOGY Co., Ltd., Beijing (CN)

( * ) Notice: Subject to any disclaimer, the term of this patent is extended or adjusted under 35 U.S.C. 154(b) by 0 days.

(21) Appl. No.: 14/123,398

(22) PCT Filed: Nov. 23, 2012

(86) PCT No.: PCT/CN2012/085197
§ 371 (c)(1),
(2) Date: Dec. 2, 2013

(87) PCT Pub. No.: WO2014/005392
PCT Pub. Date: Jan. 9, 2014

(65) Prior Publication Data
US 2014/0350136 A1    Nov. 27, 2014

(30) Foreign Application Priority Data

Jul. 4, 2012    (CN) .......................... 2012 1 0230412

(51) Int. Cl.
| | | |
|---|---|---|
| C07C 67/26 | (2006.01) | |
| C09J 4/00 | (2006.01) | |
| G02F 1/1341 | (2006.01) | |
| C07C 69/54 | (2006.01) | |
| G02F 1/1339 | (2006.01) | |
| C08F 222/10 | (2006.01) | |

(52) U.S. Cl.
CPC ................ *C07C 69/54* (2013.01); *C07C 67/26* (2013.01); *C08F 222/1006* (2013.01); *C09J 4/00* (2013.01); *G02F 1/1339* (2013.01); *G02F 2001/13415* (2013.01)

(58) Field of Classification Search
CPC ........... C08F 222/1006; C08F 222/102; C08F 222/20; C08F 222/14; C08F 222/12; C09J 4/00; C07C 67/00; C07C 67/03; C07C 67/24; C07C 67/26; C07C 69/52; C07C 69/54; C07C 69/5333
See application file for complete search history.

(56) References Cited

U.S. PATENT DOCUMENTS 8,092,981 B2    1/2012  Kang et al.
8,163,835 B2    4/2012  Park et al.

FOREIGN PATENT DOCUMENTS

| CN | 101392154 A | 3/2009 |
| CN | 101417948 A | 4/2009 |
| CN | 101477308 A | 7/2009 |

OTHER PUBLICATIONS

PCT International Search Report (Chinese language), for PCT Application No. PCT/CN2012/085197, 11 pages.
English translation of PCT International Search Report, for PCT Application No. PCT/CN2012/085197, 2 pages.
PCT International Preliminary Report on Patentability, for PCT Application No. PCT/CN2012/085197; ten (10) pages.
Shi, Tianlei et al., The Research of Sealant Used in ODF Process, Optoelectronic Technology, Sep. 2011, vol. 31, No. 3, pp. 211-214.
English abstract of: Shi, Tianlei et al., The Research of Sealant Used in ODF Process, Optoelectronic Technology, Sep. 2011, vol. 31, No. 3, pp. 211-214.
Wang, Hongyu et al., The Exploitation of Sealant Material Used in TFT LCD One Drop Filling (ODF) Process, Essays on Countrywide Radiation Curing Forum, Nov. 2006, pp. 99-110.
English abstract of: Wang, Hongyu et al., The Exploitation of Sealant Material Used in TFT LCD One Drop Filling (ODF) Process, Essays on Countrywide Radiation Curing Forum, Nov. 2006, pp. 99-110.
PCT International Preliminary Report on Patentability for PCT/CN2012/085197; ten (10) pages.

(Continued)

*Primary Examiner* — Sanza McClendon

(57) ABSTRACT

The disclosure provides a benzene ring containing compound, sealing gel, a process for preparing the same and use thereof. The compound has the following Formula (I), wherein $R_1$ and $R_2$ are the same or different, and represent alkyls of 1~4 carbon atoms, respectively. The sealing gel of the disclosure comprises one or more compounds as shown by Formula (I). The sealing gel of the disclosure not only has high binding strength to a glass substrate, but also has a good binding performance to the oriented film, thereby preventing the drop of the binding performance between the colored film substrate and the array substrate, while also decreasing the contamination of external impurities to the liquid crystals in the box.

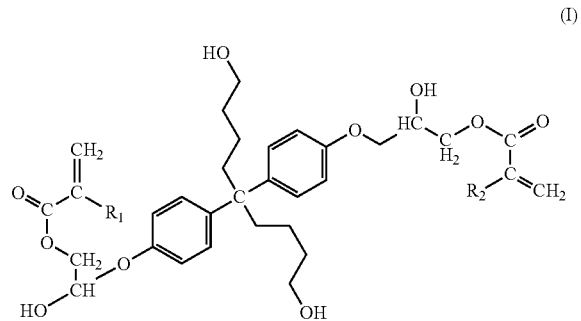

13 Claims, 1 Drawing Sheet

(56) References Cited

OTHER PUBLICATIONS

First Office Action dated Nov. 5, 2013 issued by State Intellectual Property Office of the People's Republic of China in connection with Chinese counterpart application, Chinese National Application No. 201210230412.5.
English translation of First Office Action dated Nov. 5, 2013 issued by State Intellectual Property Office of the People's Republic of China in connection with Chinese counterpart application, Chinese National Application No. 201210230412.5.
Notification to Grant the Patent Right dated Jan. 29, 2014 issued by State Intellectual Property Office of the People's Republic of China in connection with Chinese counterpart application, Chinese National Application No. 201210230412.5.
English translation of Notification to Grant the Patent Right dated Jan. 29, 2014 issued by State Intellectual Property Office of the People's Republic of China in connection with Chinese counterpart application, Chinese National Application No. 201210230412.5.
English machine translation of Chinese Patent Document No. CN 101417948 A (above), from machine translation feature of LexisNexis TotalPatent.
English translation of Abstract of Chinese Patent Document No. CN 101417948 A (above).

BENZENE RING CONTAINING COMPOUND, SEALING GEL, PROCESS FOR PREPARING SAME AND USE THEREOF

CROSS REFERENCE TO RELATED APPLICATIONS

This application is based on International Application No. PCT/CN2012/085197 filed on Nov. 23, 2012, which claims priority to Chinese National Application No. 201210230412.5 filed on Jul. 4, 2012, the contents of which are incorporated herein by reference.

TECHNICAL FIELD

The disclosure relates to a benzene ring containing compound, sealing gel, a process for preparing the same and use thereof.

BACKGROUND

ODF (one drop filling) process is a key step in the process for manufacturing the liquid crystal panel. As shown in FIG. 1, sealing gel 3 is applied to a array substrate 1, liquid crystals are dropped on the colored film substrate 2, oriented films 4 are applied to both the array substrate 1 and the colored film substrate 2 and the manufacture of the liquid crystal box is finished by aligning the array substrate 1 and the colored film substrate 2. During the manufacturing process, the main function of the sealing gel 3 is to bind the array substrate 1 and the colored film substrate 2. However, in an actual process, as shown in FIG. 2, sometimes the sealing gel 3 partially overlaps with the oriented film 4 after the alignment. In the overlapping region, the sealing gel 3 cannot directly contact with the array substrate 1 or the colored film substrate 2, causing a significant drop of the binding performance between the array substrate 1 and the colored film substrate 2, making them easier to peel off. Moreover, due to the significant drop of the binding performance between the array substrate 1 and the colored film substrate 2, it results in that external impurities easily enter into the liquid crystal box at the interface where the sealing gel 3 overlaps with the oriented film 4 and contaminate the liquid crystals in the box, thereby severely affecting the quality of the liquid crystal panel.

To address the aforementioned issues, a skilled artisan on one hand focuses on changing the edge structure to avoid the overlapping of the sealing gel 3 and the oriented film 4, and on the other hand controls the printing precision of the oriented film and the spreading width of the sealing gel, respectively. However, both means are merely applicable to the manufacture of large scale liquid crystal panels. For small scale products (e.g., the liquid crystal display screen of cellular phones), due to limit of space, currently the overlapping of the sealing gel 3 and the oriented film 4 still cannot be avoided.

SUMMARY

In view of the aforementioned issues existing in the prior art, the disclosure provides a compound and a process for preparing the same, as well as sealing gel that contains the compound, a process for preparing the same, and use thereof. Specific embodiments are as follows.

A compound as shown by the following Formula (I)

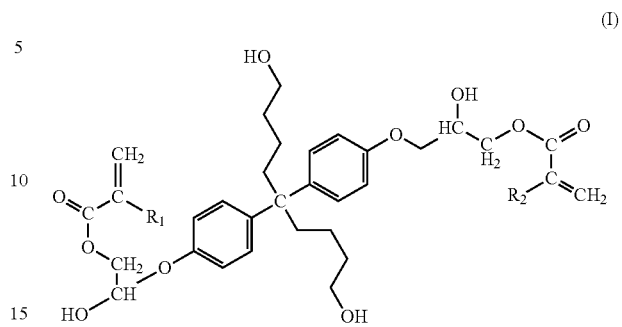

wherein $R_1$ and $R_2$ are the same or different, $R_1$ can represent an alkyl of 1~4 carbon atoms, and $R_2$ can represent an alkyl of 1~4 carbon atoms.

The disclosure further relates to a sealing gel which comprises one or more compounds as shown by Formula (I),

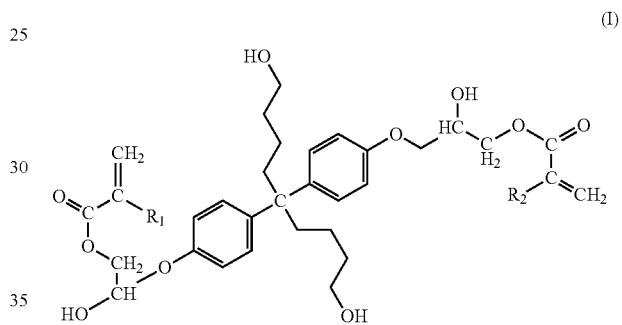

wherein each $R_1$ and $R_2$ are the same or different, $R_1$ can represent an alkyl of 1~4 carbon atoms, for example, represent methyl or t-butyl, $R_2$ can represent an alkyl of 1~4 carbon atoms, for example, represent methyl or t-butyl. Furthermore, in the sealing gel, when the various compounds as shown by Formula (I) are taken as a whole, the ratio of the total mole number of methyl to the total mole number of t-butyl can be 9:1~1:1, for example, 7:3.

The sealing gel in the disclosure can further comprise a photoinitiator. The photoinitiator can be selected from commonly used photoinitiators in the art, for example, alkyl phenylketones such as α,α-diethoxyacetophenone, α-hydroxyalkyl phenylketone, α-aminoalkyl phenylketone and the like. It may further include a diluent. The diluent can be selected from commonly used diluents in the art, for example, epoxypropane butyl ether and diglycidyl ether.

In the sealing gel of the disclosure, the mass percentage of the compounds as shown by Formula (I) (that is, taking the various compounds as shown by Formula (I) as a whole) can be 75~85%, the mass percentage of the photoinitiator can be 1~10%, and the rest can be the diluent or other substances added according to need, for example, glass microspheres, elastic small balls and the like for supporting the thickness of the box.

The disclosure further provides a process for preparing the compounds as shown in the aforementioned Formula (I), comprising reacting the compound as shown by the following Formula (II) and the compound as shown by Formula (III) to obtain the compound as shown in the aforementioned Formula (I),

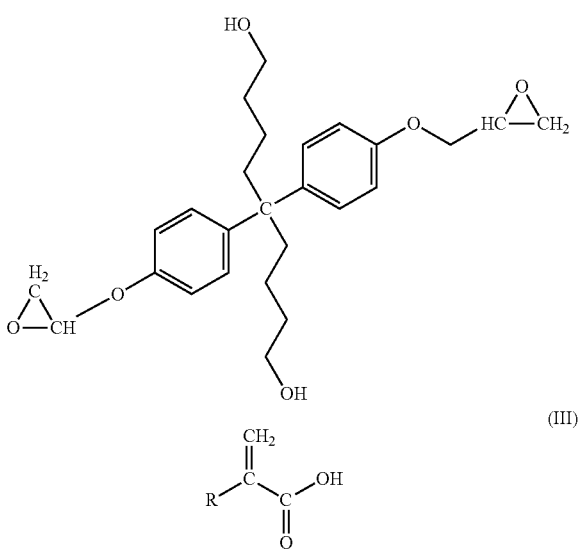

wherein R represents an alkyl of 1~4 carbon atoms, for example, represent methyl or t-butyl.

The aforementioned preparation process can in particular comprise the following steps:
(1) mixing the compound as shown by Formula (II) and a polymerization inhibitor to form Mixture 1;
(2) mixing the compound as shown by Formula (III) and a catalyst to form Mixture 2;
(3) dropping Mixture 2 into Mixture 1 under agitation at 40~100° C.; and
(4) after the completion of dropping, continuing the reaction at 80~120° C. for another 6~10 hours.

The disclosure further relates to the use of the aforementioned sealing gel in the manufacture of a display device. For example, the sealing gel may be used in the process of manufacturing a liquid crystal panel.

The sealing gel of the disclosure not only has high binding strength to a glass substrate, but also has a good binding performance to the oriented film, thereby preventing the drop of the binding performance between the colored film substrate and the array substrate, while also decreasing the contamination of external impurities to the liquid crystals in the box. Moreover, as compared to the one hour of heat curing time required for the existing sealing gel, the sealing gel of the disclosure has the advantage of rapid curing, thereby increasing the process efficiency and reducing the process cost. By utilizing the process for preparing sealing gel of the disclosure, not only the synthetic rate can be improved, but also the water resistance and the liquid crystal impact resistance can be improved due to the introduction of t-butyl.

BRIEF DESCRIPTION OF THE DRAWINGS

In order to more clearly illustrate the embodiments of the disclosure, the figures of the examples are briefly introduced below. It is obvious that the figures in the following description merely relates to a few examples of the disclosure but does not limit the disclosure.

DETAILED DESCRIPTION

Figure 1:
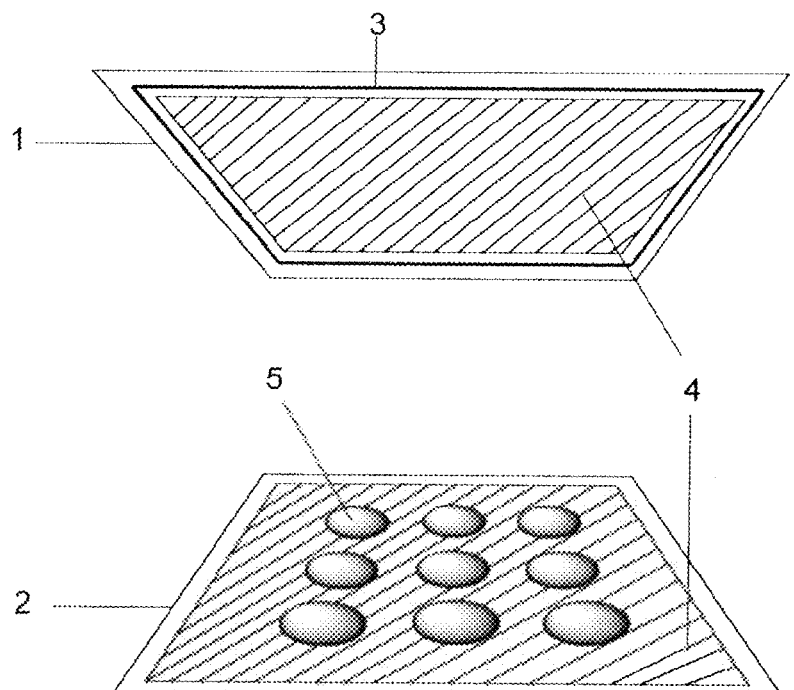
FIG. 1 is a schematic diagram representing the status of the array substrate and the colored film substrate before alignment.

In order to make the purpose, technical solutions and advantages of the disclosure more obvious, the technical solutions of the disclosure are described in a clear and complete manner in light of the figures of the disclosure. It is obvious that the examples described are merely a portion of examples of the disclosure, rather than all examples. All other examples obtained by a skilled artisan on the basis of the examples of the disclosure described without resorting to inventive work are within the scope of the disclosure.

The disclosure provides the compound as shown by the following Formula (I),

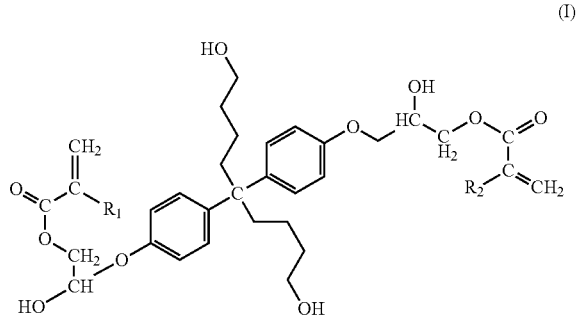

wherein $R_1$ and $R_2$ are the same or different, $R_1$ can represent an alkyl of 1~4 carbon atoms, $R_2$ can represent an alkyl of 1~4 carbon atoms.

The alkyl of 1~4 carbon atoms are for example, methyl, ethyl, propyl, isopropyl, butyl, isobutyl, t-butyl, for example, methyl or t-butyl.

The disclosure further relates to sealing gel which comprises one or more compounds as shown by Formula (I),

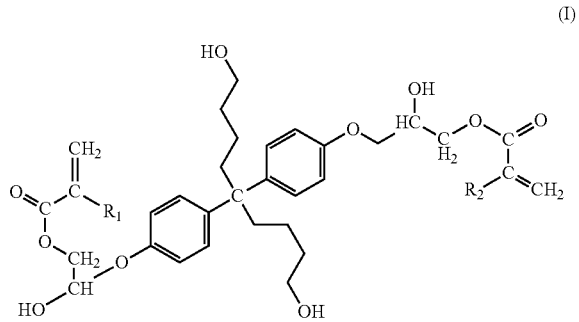

wherein each $R_1$ and $R_2$ are the same or different, $R_1$ can represent an alkyl of 1~4 carbon atoms, $R_2$ can represent an alkyl of 1~4 carbon atoms.

The alkyl of 1~4 carbon atoms are for example, methyl, ethyl, propyl, isopropyl, butyl, isobutyl, t-butyl, for example, methyl or t-butyl. Moreover, in Formula (I) (that is, in all the compounds as shown by Formula (I) contained in the sealing gel of the disclosure), the ratio of the total mole number of methyl to the total mole number of t-butyl can be 9:1~1:1, for example, 7:3.

The sealing gel of the disclosure not only has high binding strength to a glass substrate, but also has a good binding performance to the oriented film, thereby preventing the drop of the binding performance between the colored film substrate and the array substrate, while also decreasing the contamination of external impurities to the liquid crystals in the box. Moreover, as compared to the one hour of heat curing time required for the existing sealing gel, the sealing gel of the disclosure has the advantage of rapid curing, thereby increasing the process efficiency and reducing the process cost.

The sealing gel in the disclosure can further comprise a photoinitiator.

The photoinitiator can be selected from commonly used photoinitiators in the art, for example, α,α-diethoxyacetophenone, α-hydroxyalkyl phenylketone, α-aminoalkyl phenylketone and the like.

For example, the sealing gel of the disclosure may further include a diluent. The diluent can be selected from commonly used diluents in the art, for example, epoxypropane butyl ether and diglycidyl ether.

In the sealing gel of the disclosure, the mass percentage of the compounds as shown by Formula (I) (that is, taking the various compounds as shown by Formula (I) as a whole) can be 75~85%, the mass percentage of the photoinitiator can be 1~10%, and the rest can be the diluent or other substances added according to need, for example, glass microspheres, elastic small balls and the like for supporting the thickness of the box.

The disclosure further provides a process for preparing the compounds as shown in the aforementioned Formula (I), comprising reacting the compound as shown by the following Formula (II) and the compound as shown by Formula (III) to obtain the compound as shown in the aforementioned Formula (I),

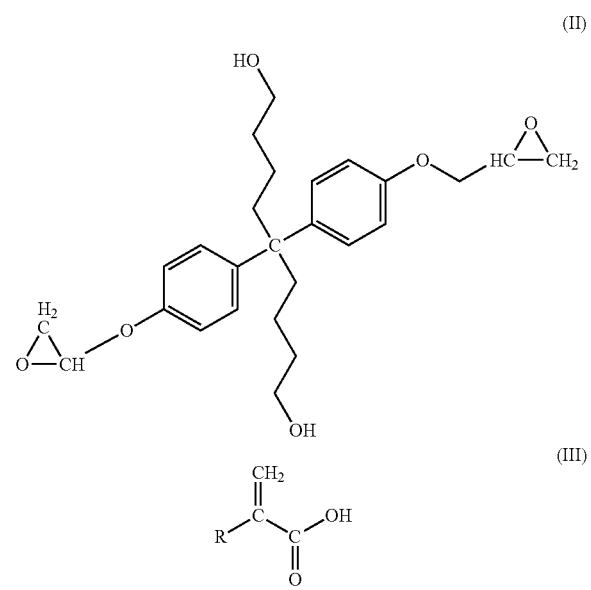

wherein R represents alkyl of 1~4 carbon atoms.

The alkyl of 1~4 carbon atoms are for example, methyl, ethyl, propyl, isopropyl, butyl, isobutyl, t-butyl, for example, methyl or t-butyl.

The aforementioned preparation process can in particular comprise the following steps:

(1) mixing the compound as shown by Formula (II) and a polymerization inhibitor to form Mixture 1, wherein the polymerization inhibitor can be a commonly used polymerization inhibitor, for example, p-hydroxylanisole;

(2) mixing the compound as shown by Formula (III) and a catalyst to form Mixture 2, wherein the catalyst can be a commonly used catalyst for polymerization, for example, tetraethyl ammonium bromide;

(3) dropping Mixture 2 into Mixture 1 under agitation at 40~100° C., for example, slowly dropping Mixture 2 (for example, at a rate of 1~2 drops per second) under agitation at 70~100° C. into Mixture 1; and (4) after the completion of dropping, continuing the reaction at 80~120° C. for another 6~10 hours, for example, continuing the reaction at 100~120° C. for another 8~10 hours.

By utilizing the process for preparing sealing gel of the disclosure, not only the synthetic rate can be improved, but also the water resistance and the liquid crystal impact resistance can be improved due to the introduction of t-butyl.

The disclosure further relates to the use of the aforementioned sealing gel in the manufacture of a display device. For example, the sealing gel may be used in the process of manufacturing a liquid crystal panel.

As to the liquid crystal panel manufactured utilizing the sealing gel of the disclosure, because the binding performance between the array substrate and the colored film substrate are greatly improved, it is difficult for the external impurities to enter into the liquid crystal box, thereby enabling the improvement of the quality of the liquid crystal panel.

The disclosure is illustrated in details below in relation to specific examples, but the disclosure is not limited to these examples.

The p-hydroxylanisole used in the following examples is produced by Beijing Chemical Works. The methacrylic acid and t-butylacrylic acid are produced by Guangzhou Tianzhong Chemical Co. Ltd. The tetraethyl ammonium bromide is produced by Yancheng Longsheng Chemical Co. Ltd. The photoinitiators and diluents are produced by Tianjin Tianjiao Chemical Co. Ltd. The compound as shown by Formula (II) is produced by Guangzhou Dute Chemical. It should be noted that the materials used in the disclosure are not limited to the products of the aforementioned manufacturers.

EXAMPLE 1

Preparation of the Compound as Shown by Formula (I)

To a 300 ml four necked flask inserted with an agitator, a condenser, a thermometer and a dropping funnel, 100 g of the compound as shown by the following Formula (II) and 0.05 g p-hydroxylanisole as the polymerization inhibitor are added, and 32 g of methacrylic acid, 21 g of t-butylacrylic acid, and 1.5 g of tetraethyl ammonium bromide are added into the dropping funnel for thoroughly mixing. The four necked flask is heated to 70° C. Under agitation, the dropping funnel is turned on and the mixture in it is dropped at the rate of 1 drop per second. After the completion of dropping, the four necked flask is heated to 100° C. for 8 h of reaction. The reaction products are obtained after cooling.

It should be noted that the products are a mixture of the various compounds as shown by Formula (I), that is, the resultant products comprise the compounds of Formula (I) wherein both $R_1$ and $R_2$ are methyl, both $R_1$ and $R_2$ are t-butyl, and $R_1$ and $R_2$ are different and are methyl and t-butyl, respectively. Moreover, the ratio of the total mole number of methyl to the total mole number of t-butyl in the reaction products is about 7:3.

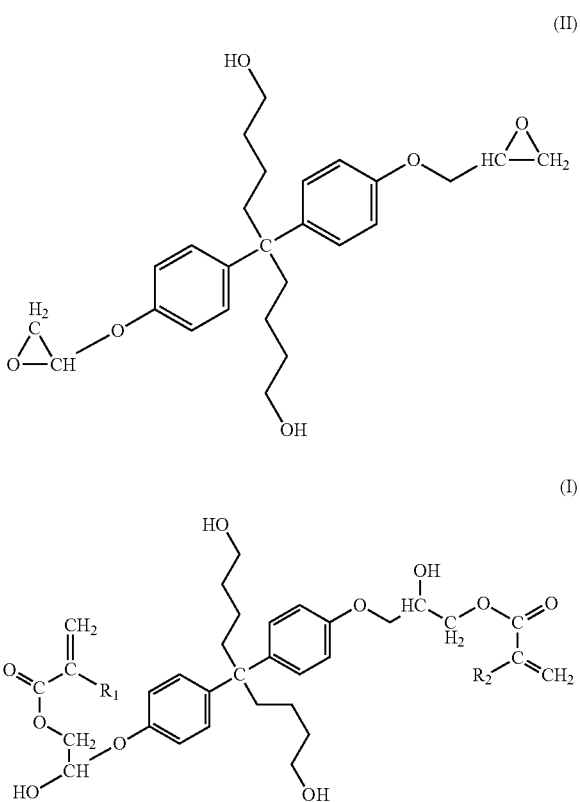

The IR (KBr) of the compound as shown by Formula (I) is: 3500 cm$^{-1}$ (hydroxy's characteristic absorption peak), 1455 cm$^{-1}$, 1506 cm$^{-1}$, 1572 cm$^{-1}$ and 1614 cm$^{-1}$ (benzene ring's characteristic absorption peaks), 1250 cm$^{-1}$ (aryl ether's absorption peak), 844 cm$^{-1}$ and 1535 cm$^{-1}$ (bisphenol A backbone's stretching vibration absorption peak), and 915 cm$^{-1}$ (epoxy's characteristic absorption peak).

The IR (KBr) of the products resulted in Example 1: 3500 cm$^{-1}$ (hydroxy's characteristic absorption peak), 1640 cm$^{-1}$ (carbon carbon double bond's absorption peak), and 1730 cm$^{-1}$ (ester carbonyl's absorption peak).

In the infrared spectra of the products obtained in Example 1, the epoxy's absorption peak at 915 cm$^{-1}$ disappears, and the hydroxy's absorption band at 3500 cm$^{-1}$ widens and deepens, indicating that ring opening occurs to the epoxyethane to form a hydroxyl. Therefore, it is known that the compound as shown by Formula (I) is generated.

Preparation of the Sealing Gel 85 parts by weight of the products obtained in Example 1, 10 parts by weight of α,α-diethoxyacetophenone as the photoinitiator and 5 parts by weight of epoxypropane butyl ether as the diluent are mixed to obtain the sealing gel 1 of the disclosure.

The sealing gel 1 is irradiated using a 3000 mJ UV lamp for 18 s, and heated at 120° C. for 10 min. The curing rate of the sealing gel is measured using a Fourier infrared spectroscopy. The result shows that the curing rate is higher than 90%.

EXAMPLE 2

Preparation of the Compound as Shown by Formula (I)

To a 300 ml four necked flask inserted with an agitator, a condenser, a thermometer and a dropping funnel, 100 g of the compound as shown by the following Formula (II) and 0.05 g p-hydroxylanisole as the polymerization inhibitor are added, and 127 g of methacrylic acid, 21 g of t-butylacrylic acid, and 1.5 g of tetraethyl ammonium bromide are added into the dropping funnel for thoroughly mixing. The four necked flask is heated to 70° C. Under agitation, the dropping funnel is turned on and the mixture in it is dropped at the rate of 1 drop per second. After the completion of dropping, the four necked flask is heated to 100° C. for 8 h of reaction. The reaction products are obtained after cooling.

It should be noted that the products are a mixture of the various compounds as shown by Formula (I), that is, the resultant products comprise the compounds of Formula (I) wherein both $R_1$ and $R_2$ are methyl, both $R_1$ and $R_2$ are t-butyl, and $R_1$ and $R_2$ are different and are methyl and t-butyl, respectively. Moreover, the ratio of the total mole number of methyl to the total mole number of t-butyl in the reaction products is about 9:1.

The IR (KBr) of the compound as shown by Formula (II): 3500 cm$^{-1}$ (hydroxy's characteristic absorption peak), 1455 cm$^{-1}$, 1506 cm$^{-1}$, 1572 cm$^{-1}$ and 1614 cm$^{-1}$ (benzene ring's characteristic absorption peak), 1250 cm$^{-1}$ (aryl ether's absorption peak), 844 cm$^{-1}$ and 1535 cm$^{-1}$ (bisphenol A backbone's stretching vibration absorption peak), and 915 cm$^{-1}$ (epoxy's characteristic absorption peak).

The IR (KBr) of the products resulted in Example 2: 3500 cm$^{-1}$ (hydroxy's characteristic absorption peak), 1640 cm$^{-1}$ (carbon carbon double bond's absorption peak), and 1730 cm$^{-1}$ (ester carbonyl's absorption peak).

In the infrared spectra of the products obtained in Example 2, the epoxy's absorption peak at 915 cm$^{-1}$ disappears, and the hydroxy's absorption band at 3500 cm$^{-1}$ widens and deepens, indicating that ring opening occurs to the epoxyethane to form a hydroxyl. Therefore, it is known that the compound as shown by Formula (I) is generated.

Preparation of the Sealing Gel 75 parts by weight of the products obtained in Example 2, 5 parts by weight of α,α-diethoxyacetophenone as the photoinitiator and 20 parts by weight of epoxypropane butyl ether as the diluent are mixed to obtain the sealing gel 2 of the disclosure.

The sealing gel 2 is irradiated using a 3000 mJ UV lamp for 20 s, and heated at 120° C. for 10 min. The curing rate of the sealing gel is measured using a Fourier infrared spectroscopy. The result shows that the curing rate is higher than 90%.

EXAMPLE 3

Preparation of the Compound as Shown by Formula (I)

To a 300 ml four necked flask inserted with an agitator, a condenser, a thermometer and a dropping funnel, 100 g of the compound as shown by the following Formula (II) and 0.05 g p-hydroxylanisole as the polymerization inhibitor are added, and 14 g of methacrylic acid, 21 g of t-butylacrylic acid, and 1.5 g of tetraethyl ammonium bromide are added into the dropping funnel for thoroughly mixing. The four necked flask is heated to 70° C. Under agitation, the dropping funnel is turned on and the mixture in it is dropped at the rate of 1 drop per second. After the completion of dropping, the four necked flask is heated to 100° C. for 8 h of reaction. The reaction products are obtained after cooling.

It should be noted that the products are a mixture of the various compounds as shown by Formula (I), that is, the resultant products comprise the compounds of Formula (I) wherein both $R_1$ and $R_2$ are methyl, both $R_1$ and $R_2$ are t-butyl, and $R_1$ and $R_2$ are different and are methyl and t-butyl, respectively. Moreover, the ratio of the total mole number of methyl to the total mole number of t-butyl in the reaction products is about 1:1.

The IR (KBr) of the compound as shown by Formula (II): 3500 $cm^{-1}$ (hydroxy's characteristic absorption peak), 1455 $cm^{-1}$, 1506 $cm^{-1}$, 1572 $cm^{-1}$ and 1614 $cm^{-1}$ (benzene ring's characteristic absorption peak), 1250 $cm^{-1}$ (aryl ether's absorption peak), 844 $cm^{-1}$ and 1535 $cm^{-1}$ (bisphenol A backbone's stretching vibration absorption peak), and 915 $cm^{-1}$ (epoxy's characteristic absorption peak).

The IR (KBr) of the products resulted in Example 3: 3500 $cm^{-1}$ (hydroxy's characteristic absorption peak), 1640 $cm^{-1}$ (carbon carbon double bond's absorption peak), and 1730 $cm^{-1}$ (ester carbonyl's absorption peak).

In the infrared spectra of the products obtained in Example 3, the epoxy's absorption peak at 915 $cm^{-1}$ disappears, and the hydroxy's absorption band at 3500 $cm^{-1}$ widens and deepens, indicating that ring opening occurs to the epoxyethane to form a hydroxyl. Therefore, it is known that the compound as shown by Formula (I) is generated.

Preparation of the Sealing Gel 80 parts by weight of the products obtained in Example 3, 3 parts by weight of α,α-diethoxyacetophenone as the photoinitiator and 17 parts by weight of epoxypropane butyl ether as the diluent are mixed to obtain the sealing gel 3 of the disclosure.

The sealing gel 3 is irradiated using a 3000 mJ UV lamp for 25 s, and heated at 120° C. for 15 min. The curing rate of the sealing gel is measured using a Fourier infrared spectroscopy. The result shows that the curing rate is higher than 90%.

EXAMPLE 4

Preparation of the Compound as Shown by Formula (I)

To a 300 ml four necked flask inserted with an agitator, a condenser, a thermometer and a dropping funnel, 100 g of the compound as shown by the following Formula (II) and 0.05 g p-hydroxylanisole as the polymerization inhibitor are added, and 32 g of methacrylic acid, 21 g of t-butylacrylic acid, and 1.5 g of tetraethyl ammonium bromide are added into the dropping funnel for thoroughly mixing. The four necked flask is heated to 70° C. Under agitation, the dropping funnel is turned on and the mixture in it is dropped at the rate of 1 drop per second. After the completion of dropping, the four necked flask is heated to 100° C. for 8 h of reaction. The reaction products are obtained after cooling. It should be noted that the products are a mixture of the various compounds as shown by Formula (I), that is, the resultant products comprise the compounds of Formula (I) wherein both $R_1$ and $R_2$ are methyl, both $R_1$ and $R_2$ are t-butyl, and $R_1$ and $R_2$ are different and are methyl and t-butyl, respectively. Moreover, the ratio of the total mole number of methyl to the total mole number of t-butyl in the reaction products is about 7:3.

The IR (KBr) of the compound as shown by Formula (II): 3500 $cm^{-1}$ (hydroxy's characteristic absorption peak), 1455 $cm^{-1}$, 1506 $cm^{-1}$, 1572 $cm^{-1}$ and 1614 $cm^{-1}$ (benzene ring's characteristic absorption peak), 1250 $cm^{-1}$ (aryl ether's absorption peak), 844 $cm^{-1}$ and 1535 $cm^{-1}$ (bisphenol A backbone's stretching vibration absorption peak), and 915 $cm^{-1}$ (epoxy's characteristic absorption peak).

The IR (KBr) of the products resulted in Example 4: 3500 $cm^{-1}$ (hydroxy's characteristic absorption peak), 1640 $cm^{-1}$ (carbon carbon double bond's absorption peak), and 1730 $cm^{-1}$ (ester carbonyl's absorption peak).

In the infrared spectra of the products obtained in Example 4, the epoxy's absorption peak at 915 $cm^{-1}$ disappears, and the hydroxy's absorption band at 3500 $cm^{-1}$ widens and deepens, indicating that ring opening occurs to the epoxyethane to form a hydroxyl. Therefore, it is known that the compound as shown by Formula (I) is generated.

Preparation of the Sealing Gel 85 parts by weight of the products obtained in Example 4, 1 part by weight of α,α-diethoxyacetophenone as the photoinitiator and 14 parts by weight of epoxypropane butyl ether as the diluent are mixed to obtain the sealing gel 4 of the disclosure.

The sealing gel 4 is irradiated using a 3000 mJ UV lamp for 18 s, and heated at 120° C. for 15 min. The curing rate of the sealing gel is measured using a Fourier infrared spectroscopy. The result shows that the curing rate is higher than 90%.

Peeling Experiment

The following peeling of experiment is conducted on the sealing gel 1~4 in Examples 1~4 of the disclosure and the commercial available sealing gel UR-2920 (manufactured by Mitsui Chemical) as the comparative example. It should be noted, the UR-2920 sealing gel contains by weight of about 85% binder (which serves the same role in the sealing gel as the compound as shown by Formula (I) in the sealing gel of the disclosure) and around 10% initiator.

Sealing gel is spread at 5 mm from the edges around a 40 mm×45 mm white glass plate with a cross section area of 4000±400 $um^2$. Then the white glass plate is aligned under vacuum with another 36 mm×36 mm white glass plate, so that the gap between the two glass plates is 5 um. The peeling strength is measured after UV exposure (5000 $mJ/cm^2$) and heat curing (120° C., 1 hour). The specific procedure of the measurement is as follows: forces are applied constantly by manipulators perpendicularly from the four corners of the 40 mm×45 mm white glass plate at a constant rate of 5 mm/min so that the two glass plates are about to peel. The force then applied is recorded and the peeling strength is calculated. For each sealing gel, three experiments are conducted, and their average is used as the peeling strength of the sealing gel at a certain corner of the glass plate. The results are shown in Table 1.

TABLE 1

| | Peeling Strength (N/mm) | | | |
|---|---|---|---|---|
| Sealing gel | Corner 1 | Corner 2 | Corner 3 | Corner 4 |
| Example 1 | 15.2 | 14.4 | 15.1 | 15.2 |
| Example 2 | 14.0 | 13.6 | 13.8 | 14.2 |
| Example 3 | 12.9 | 13.8 | 14.6 | 12.8 |
| Example 4 | 11.8 | 12.2 | 12.6 | 11.3 |
| Comparative Example | 10.6 | 9.4 | 10.7 | 10.8 |

Figure 2:
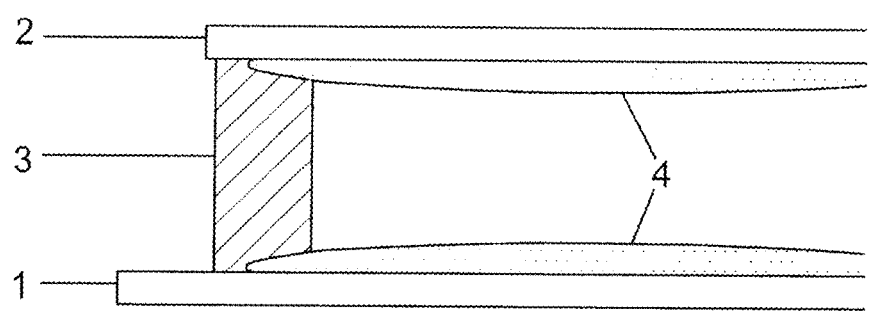
FIG. 2 is a schematic diagram representing the partial overlapping of the oriented film and the sealing gel after alignment in the prior art.

From the results in Table 1, it can be seen that the sealing gel prepared in the disclosure has a higher binding strength than the prior art sealing gel and can facilitate the issue of the drop of binding performance caused by the overlapping of the sealing gel and the oriented film in FIG. 2.

The aforementioned are merely exemplary embodiments of the disclosure and are not limiting the scope of the disclosure, which is determined by the appended claims.

The invention claimed is:

1. A compound as shown by the following Formula (I),

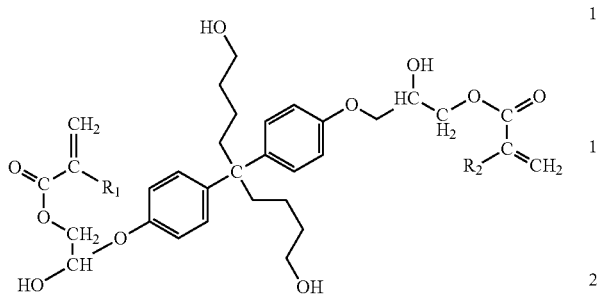

(I)

wherein $R_1$ and $R_2$ are the same or different, $R_1$ represents an alkyl of 1~4 carbon atoms, and $R_2$ represents an alkyl of 1~4 carbon atoms.

2. A sealing gel comprising one or more compounds as shown by Formula (I),

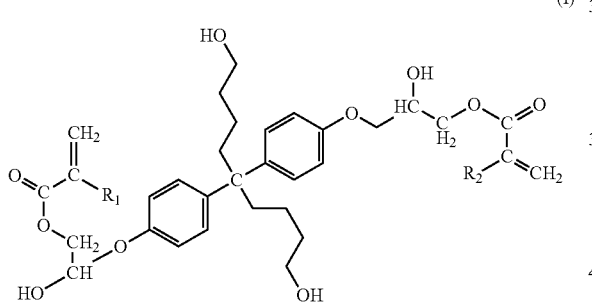

(I)

wherein each $R_1$ and $R_2$ are the same or different, $R_1$ represents an alkyl of 1~4 carbon atoms, and $R_2$ represents an alkyl of 1~4 carbon atoms.

3. The sealing gel according to claim 2, wherein R1 represents methyl or t-butyl, and R2 represents methyl or t-butyl, and by Formula (I), the ratio of the total mole number of methyl represented by R1 and R2 to the total mole number of t-butyl represented by R1 and R2 is 9:1~1:1.

4. The sealing gel according to claim 3, wherein the ratio of the mole number of methyl represented by R1 and R2 to the mole number of t-butyl represented by R1 and R2 is 7:3.

5. The sealing gel according to claim 2, wherein the sealing gel further comprises a photoinitiator.

6. The sealing gel according to claim 5, wherein the mass percentage of the compounds as shown by Formula (I) is 75~85%, and the mass percentage of the photoinitiator is 1~10%.

7. The sealing gel according to claim 5, wherein the photoinitiator is an alkyl phenylketone.

8. A process for preparing the compound according to claim 1, comprising reacting the compound as shown by the following Formula (II) and the compound as shown by Formula (III),

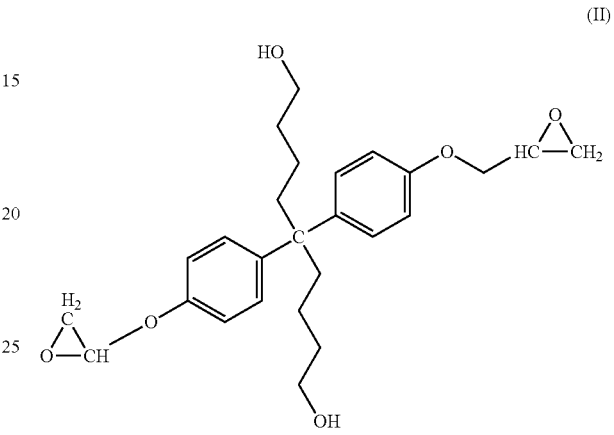

wherein R represents an alkyl of 1~4 carbon atoms.

9. The process according to claim 8 comprising the steps of
(1) mixing the compound as shown by Formula (II) and a polymerization inhibitor to form Mixture 1;
(2) mixing the compound as shown by Formula (III) and a catalyst to form Mixture 2;
(3) dropping Mixture 2 into Mixture 1 under agitation at 40~100° C.; and
(4) after the completion of dropping, continuing the reaction at 80~120° C. for another 6~10 hours.

10. The process according to claim 9, wherein the polymerization inhibitor is p-hydroxylanisole.

11. The process according to claim 9, wherein the catalyst is tetraethyl ammonium bromide.

12. A method of using the sealing gel according to claim 2 in the manufacture of a display device, wherein the sealing gel is used to bind an array substrate and a colored film substrate in the display device.

13. The sealing gel according to claim 6, wherein the photoinitiator is an alkyl phenylketone.

* * * * *